US012723015B2

(12) United States Patent
Geissler

(10) Patent No.: US 12,723,015 B2
(45) Date of Patent: Sep. 1, 2026

(54) TWO-STAGE PREPARATION PROCESS FOR α,β-ETHYLENICALLY UNSATURATED CARBOXYLIC ACIDS AND PLANT FOR THE PURPOSE

(71) Applicant: BASF SE, Ludwigshafen am Rhein (DE)

(72) Inventor: Tobias Geissler, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 633 days.

(21) Appl. No.: 18/037,571

(22) PCT Filed: Oct. 25, 2021

(86) PCT No.: PCT/EP2021/079553

§ 371 (c)(1),
(2) Date: May 18, 2023

(87) PCT Pub. No.: WO2022/106158

PCT Pub. Date: May 27, 2022

(65) Prior Publication Data

US 2025/0074858 A1 Mar. 6, 2025

(30) Foreign Application Priority Data

Nov. 19, 2020 (EP) .................................... 20208603

(51) Int. Cl.
*C07C 51/25* (2006.01)

(52) U.S. Cl.
CPC ........ *C07C 51/252* (2013.01); *C07C 2523/28* (2013.01)

(58) Field of Classification Search
CPC ......................... C07C 51/252; C07C 2523/28
See application file for complete search history.

(56) References Cited

U.S. PATENT DOCUMENTS 6,069,271 A 5/2000 Tanimoto et al.
8,232,425 B2 7/2012 Dieterle et al.
(Continued)

FOREIGN PATENT DOCUMENTS

DE 3338380 A1 4/1984
DE 4407020 A1 9/1994
(Continued)

OTHER PUBLICATIONS

Roget's 21st Century Thesaurus, 2005, p. 629 (Year: 2005).*
(Continued)

*Primary Examiner* — Amy C Bonaparte
*Assistant Examiner* — Derek Rhoades
(74) *Attorney, Agent, or Firm* — Faegre Drinker Biddle & Reath LLP

(57) ABSTRACT

The invention relates to a process for preparing α,β-ethylenically unsaturated carboxylic acids by two-stage catalytic gas phase oxidation of alkenes, in which a gas stream (1) containing at least one alkene, in a first reactor (A) in the presence of oxygen, is subjected to a first catalytic oxidation reaction over a first catalyst (K1) in the form of a multimetal oxide of molybdenum to obtain a gas stream (2) containing at least one α,β-ethylenically unsaturated aldehyde, the gas stream (2) containing the at least one α,β-ethylenically unsaturated aldehyde is guided through a connecting conduit (V) into a second reactor (B) and the gas stream (2) containing the at least one α,β-ethylenically unsaturated aldehyde, in the second reactor (B) in the presence of oxygen, is subjected to a second catalytic oxidation reaction over a second catalyst (K2) to obtain a gas stream (3) containing at least one α,β-ethylenically unsaturated carboxylic acid. In the process according to the invention, the gas stream (2) containing the at least one α,β-ethylenically unsaturated aldehyde is guided through an exchangeable (Continued)

structure (S) having high specific surface area which is disposed within the connecting conduit (V). The invention further relates to a corresponding plant.

15 Claims, 2 Drawing Sheets

(56) References Cited

U.S. PATENT DOCUMENTS

| | | | | |
|---|---|---|---|---|
| 2004/0138499 | A1 | 7/2004 | Buschulte et al. | |
| 2008/0021240 | A1* | 1/2008 | Tanimoto et al. | C07C 27/10 |
| 2010/0130777 | A1* | 5/2010 | Tanimoto et al. | C07C 51/16 562/545 |

FOREIGN PATENT DOCUMENTS

| | | | |
|---|---|---|---|
| EP | 0575897 | A1 | 12/1993 |
| EP | 2114562 | A1 | 11/2009 |
| WO | 02/81422 | A1 | 10/2002 |
| WO | 2008/087116 | A1 | 7/2008 |

OTHER PUBLICATIONS

International Search Report and Written Opinion received for PCT Patent Application No. PCT/EP2021/079553, mailed on Feb. 16, 2022, 17 pages (8 pages of English Translation and 9 pages of Original Document).

* cited by examiner

TWO-STAGE PREPARATION PROCESS FOR α,ß-ETHYLENICALLY UNSATURATED CARBOXYLIC ACIDS AND PLANT FOR THE PURPOSE

CROSS-REFERENCE TO RELATED APPLICATIONS

This application is a National stage application (under 35 U.S.C. § 371) of PCT/EP2021/079553, filed Oct. 25, 2021, which claims benefit of European Application No. 20208603.9, filed Nov. 19, 2020, both of which are incorporated herein by reference in their entirety.

The present invention relates to a process for producing α,β-ethylenically unsaturated carboxylic acids by two-stage catalytic gas phase oxidation of alkenes, especially to a process for two-stage oxidation of propylene to acrylic acid, and to a plant for the purpose.

Such a two-stage process for producing acrylic acid is known per se and is described, for example, in WO 02/081422 A1 and the documents cited therein.

First of all, a first reactor is supplied with propylene and molecular oxygen. The oxygen may be introduced, for example, in the form of air. In addition, it is possible to supply an inert gas, for example nitrogen. In the first reactor, propylene is converted to acrolein by catalytic oxidation. The outlet gas from the first reactor thus comprises acrolein and unconverted oxygen inter alia. This outlet gas is introduced into the second reactor, wherein acrolein and oxygen are converted to acrylic acid.

Catalysts used in the first and second reactors are catalysts suitable for the gas phase oxidation of propylene to acrolein or of acrolein to acrylic acid. A large number of catalysts suitable for the reactions mentioned have been suggested to date. Typically, multimetal oxides of molybdenum are used in industry.

In order to very substantially convert the acrolein introduced into the second reactor to acrylic acid, sufficient oxygen must also be available in the second reactor. For this purpose, there may already be so much oxygen introduced into the first reactor that sufficient oxygen still remains for the reaction in the second reactor after the conversion of propylene to acrolein. Alternatively, it is possible to supplement oxygen between the first and second reactors. Since increasing the oxygen content in a mixture of propylene and oxygen increases the explosion risk, it is advantageous to introduce only as much oxygen as required for the conversion of propylene to acrolein into the first reactor. Subsequently, as much oxygen as required for the conversion of the acrolein to acrylic acid is added between the first and second reactors.

It has been found that, in the operation of a plant executing this method, a pressure drop is found in the second reactor as the reaction gas passes through. The operation of the synthesis at elevated pressure results in losses in acrylic acid selectivity. Once the pressure drop has reached a particular degree, the reactor has to be shut down for maintenance. This operation is also called skimming. The maintenance is both time- and resource-consuming, since the shutdown time is extended by cooling and heating of the plant.

U.S. Pat. No. 6,069,271 describes a process for producing acrylic acid from propylene by two-stage catalytic oxidation using a single fixed bed shell-and-tube heat exchange reactor. A first catalyst layer is provided in the lower portion of each of the reaction tubes, a second catalyst layer in the upper portion thereof. Between those is provided an inert layer with a void ratio of 40% to 99.5%. The process is intended to prevent the problem of blockage of the reaction tubes caused by sublimed catalyst components of the first catalyst that are entrained downstream by the reaction gas stream.

It is an object of this invention to develop the process specified at the outset and the plant specified at the outset in such a way as to reduce the need for maintenance.

According to the invention, the object is achieved by a process according to claim 1 and a plant according to claim 6. Advantageous embodiments and further developments are revealed by the dependent claims.

The process of the invention for producing α,β-ethylenically unsaturated carboxylic acids by two-stage catalytic gas phase oxidation of alkenes is a process in which a) a gas stream comprising at least one alkene, in a first reactor in the presence of oxygen, is subjected to a first catalytic oxidation reaction over a first catalyst in the form of a multimetal oxide of molybdenum to obtain a gas stream comprising at least one α,β-ethylenically unsaturated aldehyde,
b) the gas stream comprising at least one α,β-ethylenically unsaturated aldehyde is directed through a connecting conduit into a second reactor and
c) the gas stream comprising at least one α,β-ethylenically unsaturated aldehyde, in the second reactor in the presence of oxygen, is subjected to a second catalytic oxidation reaction over a second catalyst to obtain a gas stream comprising at least one α,β-ethylenically unsaturated carboxylic acid.

The process comprises directing the gas stream comprising at least one α,β-ethylenically unsaturated aldehyde through an exchangeable structure with high specific surface area which is disposed in the connecting conduit.

The gas stream comprising at least one alkene comprises one or more alkenes. Suitable alkenes comprise, for example, 3 to 5 carbon atoms per molecule and are selected, for example, from propylene, 2-methylpropylene, 1-butene, 2-butene or 1-pentene. The alkene is preferably selected from propylene and 2-methylpropylene. Propylene is particularly preferred.

The gas stream comprising at least one alkene is subjected to a first catalytic oxidation reaction in the presence of oxygen. It is possible to supply an external oxygen source. Suitable external oxygen sources include, for example, oxygen, synthetic air and air. Air is particularly preferred.

The first catalytic oxidation reaction is performed in the first reactor. The first reactor is any reactor for gas phase oxidations. In a preferred embodiment, the first reactor is a fixed bed shell-and-tube heat exchange reactor. The performance of the reaction in a fixed bed shell-and-tube heat exchange reactor enables uniform removal of heat and good heat exchange.

Such fixed bed shell-and-tube heat exchange reactors typically consist of a generally cylindrical vessel accommodating a multitude of catalyst tubes (a tube bundle) in a typically vertical arrangement. Each of these catalyst tubes comprises a fixed bed arrangement of the catalytically active multimetal oxide (e.g. first catalyst in the first reactor). The ends of the catalyst tubes are secured with sealing in tube sheets, and each of them opens into a hood connected to the vessel at the upper and lower ends. Through these hoods, the gas stream flowing through the catalyst tubes is supplied and removed, such that each catalyst tube corresponds to an elongated reaction unit zone. Typically, the catalyst tubes have a wall thickness of 1 to 3 mm, an internal diameter of 20 to 30 mm, and a tube length of 2 to 4 m. Appropriately in application terms, the number of catalyst tubes accommodated in the vessel runs to at least 5000, preferably to at least 10 000. Frequently, the number of catalyst tubes accommodated in the reaction vessel is 15 000 to 30 000. Within the vessel, the catalyst tubes are normally arranged in homogeneous distribution, the distribution appropriately being selected such that the separation of the central internal axes of mutually adjacent catalyst tubes is 35 to 45 mm.

In addition, a heat exchange medium is passed through the space surrounding the catalyst tubes, in order to remove the process heat. After exiting from the vessel, the heat exchange media are brought back to their original temperature, for example in external heat exchangers, before they re-enter the reaction vessel. Suitable heat exchange media are, in particular, fluid temperature control media. It is particularly favorable to use melts of salts ("salt bath") such as potassium nitrate, potassium nitrite, sodium nitrite and/or sodium nitrate, or of low-melting metals such as sodium, mercury and alloys of different metals.

The first catalytic oxidation reaction is performed in the presence of the first catalyst.

The first catalyst takes the form of a multimetal oxide of molybdenum. Such catalysts are known per se. In one embodiment, the multimetal oxide has a stoichiometry of the general formula (I)

$$Mo_{12}Bi_aFe_bX^1_cX^2_cX^3_eX^4_fO_n \quad \text{(I)}$$

in which $X^1$=nickel and/or cobalt, $X^2$=thallium, samarium, an alkali metal and/or an alkaline earth metal, $X^3$=zinc, phosphorus, arsenic, boron, antimony, tin, cerium, lead, vanadium, chromium, niobium and/or tungsten, $X^4$=silicon, aluminum, titanium and/or zirconium, a=0.2 to 5, b=0.01 to 5, c=0 to 10, d=0 to 2, e=0 to 8, f=0 to 10, and n is a number which is determined by the valency and frequency of the elements in (I) excluding oxygen.

In preferred embodiments, the stoichiometric coefficients are as follows:

a=0.4 to 2, b=2 to 4, c=3 to 10, d=0.02 to 2, e=0 to 5, and f=0.5 or 1 to 10.

$X^1$ is preferably cobalt, $X^2$ is preferably K, Cs and/or Sr, more preferably K, $X^3$ is preferably tungsten, zinc and/or phosphorus, and $X^4$ is preferably Si. More preferably, the variables $X^1$ to $X^4$ simultaneously have the definitions given above. It is even more preferable that all stoichiometric coefficients a to f and all variables $X^1$ to $X^4$ simultaneously have the advantageous definitions given above.

In one embodiment, the catalytically active multimetal oxide has a stoichiometry of the general formula (II)

$$[Y^1_{a'}Y^2_{b'}O_{x'}]p[Y^3_{c'}Y^4_{d'}Y^5_{e'}Y^6_{f'}Y^7_{g'}Y^8_{h'}O_{y'}]q \quad \text{(II)}$$

in which $Y^1$=bismuth only, or bismuth and at least one of the elements tellurium, antimony, tin and copper, $Y^2$=molybdenum and/or tungsten, $Y^3$=an alkali metal, thallium and/or samarium, $Y^4$=an alkaline earth metal, nickel, cobalt, copper, manganese, zinc, tin, cadmium and/or mercury, $Y^5$=iron, or iron and at least one of the elements vanadium, chromium and cerium, $Y^6$=phosphorus, arsenic, boron and/or antimony, $Y^7$=a rare earth metal, titanium, zirconium, niobium, tantalum, rhenium, ruthenium, rhodium, silver, gold, aluminum, gallium, indium, silicon, germanium, lead, thorium and/or uranium, $Y^8$=molybdenum and/or tungsten, a'=0.01 to 8, b'=0.1 to 30, c'=0 to 4, d'=0 to 20, e'>0 to 20, f'=0 to 6, g'=0 to 15, h'=8 to 16, x', y' are numbers which are determined by the valency and frequency of the elements in (II) excluding oxygen, and p, q are numbers having a p/q ratio between 0.1 and 10.

Particularly advantageous catalytically active multimetal oxides of the stoichiometry (II) are those in which $Y^1$ is bismuth only.

Catalytically active multimetal oxides of stoichiometry (II) comprise three-dimensional regions of chemical composition $Y^1_{a'}Y^2_{b'}O_{x'}$, dispersed in a matrix phase of chemical composition $Y^3_{c'}Y^4_{d'}Y^5_{e'}Y^6_{f'}$, $Y^7_{g'}$, $Y^8_{h'}$, $O_{y'}$.

The production of such catalysts is described in detail in documents DE4407020 A1, EP575897 A1, DE3338380 A1 and EP2114562 A1.

Among the stoichiometries of the general formula (II), preference is given to those that conform to the general formula (IIa)

$$[Bi_{a''}Z^2_{b''}O_{x''}]p''[Z^8_{12}Z^3_{c''}Z^4_{d''}Fe_{e''}Z^5_{f''}Z^6_{g''}Z^7_{h''}O_{y''}]q'' \quad \text{(IIa)}$$

in which $Z^2$=molybdenum and/or tungsten, $Z^3$=nickel and/or cobalt, $Z^4$=thallium, an alkali metal and/or an alkaline earth metal, preferably K, Cs and/or Sr, $Z^5$=phosphorus, arsenic, boron, antimony, tin, cerium, vanadium, chromium and/or Bi, $Z^6$=silicon, aluminum, titanium and/or zirconium, preferably Si, $Z^7$=copper, silver and/or gold, $Z^8$=molybdenum and/or tungsten, a"=0.1 to 1, b"=0.2 to 2, c"=3 to 10, d"=0.02 to 2, e"=0.01 to 5, preferably 0.1 to 3, f=0 to 5, g"=0 to 10, preferably >0 to 10, more preferably 0.2 to 10 and most preferably 0.4 to 3, h"=0 to 1, x", y" are numbers which are determined by the valency and frequency of the elements in (IIa) excluding oxygen, and p", q" are numbers having a p"/q" ratio between 0.1 and 5, preferably between 0.5 and 2.

Among the catalytically active multimetal oxides of stoichiometry (IIa), preference is given to those in which $Z^2_{b''}$=$(tungsten)_{b''}$ and $Z^8_{12}$=$(molybdenum)_{12}$.

The first catalytic oxidation reaction in the first reactor is performed at a temperature in the range from 200 to 420° C., an operating pressure in the range from 2 to 3 bar absolute, and a residence time in the range from 1.5 to 2.5 seconds.

The product stream from the first catalytic oxidation reaction comprises, in addition to any unconverted portion of the alkene, at least one α,β-ethylenically unsaturated aldehyde which has been formed by partial oxidation of alkene. Thus, the partial oxidation of propylene leads to acrolein, and the partial oxidation of 2-methylpropylene to methacrolein. The α,β-ethylenically unsaturated aldehyde is preferably selected from acrolein.

The gas stream comprising at least one α,β-ethylenically unsaturated aldehyde is removed via the connecting conduit at the exit from the first reactor and introduced into the second reactor.

The gas stream comprising at least one α,β-ethylenically unsaturated aldehyde is subjected to a second catalytic oxidation reaction in the presence of oxygen. It is possible to supply an external oxygen source. Suitable external oxygen sources include, for example, oxygen, synthetic air and air. Air is particularly preferred.

The second catalytic oxidation reaction is performed in the second reactor. The second reactor is any reactor for gas phase oxidations. In a preferred embodiment, the second reactor is a fixed bed shell-and-tube heat exchange reactor. The performance of the reaction in a fixed bed shell-and-tube heat exchange reactor enables uniform removal of heat and good heat exchange.

The second catalytic oxidation reaction is performed in the presence of a second catalyst. The second catalyst takes the form of a multimetal oxide of molybdenum. Such catalysts are known per se. In one embodiment, the multimetal oxide has a stoichiometry of the general formula (III)

$$Mo_{12}V_aX^1_bX^2_cX^3_dX^4_eX^5_fX^6_gO_n \quad \text{(III)}$$

in which $X^1$=W, Nb, Ta, Cr and/or Ce, $X^2$=Cu, Ni, Co, Fe, Mn and/or Zn, $X^3$=Sb and/or Bi, $X^4$=one or more alkali metals (Li, Na, K, Rb, Cs) and/or H, $X^5$=one or more alkaline earth metals (Mg, Ca, Sr, Ba), $X^6$=Si, Al, Ti and/or Zr, a=1 to 6, b=0.2 to 4, c=0 to 18, preferably 0.5 to 18, d=0 to 40, e=0 to 2, f=0 to 4, g=0 to 40, and n is a number which is determined by the valency and frequency of the elements in (III) excluding oxygen.

Preferably, the variables should be chosen within the ranges specified with the proviso that the molar proportion of the element Mo, based on the total amount of all elements excluding oxygen in the multimetal oxide material (III), is 20 to 80 mol %, the molar ratio of Mo present in the catalytically active multimetal oxide material (III) to V, Mo/V, present in the catalytically active multimetal oxide material (III) is 15:1 to 1:1, and the corresponding molar ratio Mo/(total amount of W and Nb) is 80:1 to 1:4 (and the corresponding molar Mo/Cu ratio is 30:1 to 1:3 when the multimetal oxide material comprises Cu).

Preferred multimetal oxide catalysts (III) are those in which $X^1$=W, Nb and/or Cr, $X^2$=Cu, Ni, Co and/or Fe, $X^3$=Sb, $X^4$=Na and/or K, $X^5$=Ca, Sr and/or Ba, $X^6$=Si, Al and/or Ti, a=2.5 to 5, b=0.5 to 2, c=0.5 to 3, d=0 to 2, e=0 to 0.2, f=0 to 1, g=0 to 15, and n is a number which is determined by the valency and frequency of the elements in (III) excluding oxygen.

Preferred multimetal oxide catalysts conform to the following general stoichiometry (IIIa)

$$Mo_{12}V_aX^1_bX^2_cX^5_fX^6_gO_n \quad \text{(IIIa)}$$

in which $X^1$=W and/or Nb, $X^2$=Cu and/or Ni, $X^5$=Co and/or Sr, $X^6$=Si and/or Al, a=3 to 4.5, b=1 to 1.5, c=0.75 to 2.5, f=0 to 0.5, g=0 to 8, and n is a number which is determined by the valency and frequency of the elements in (IIIa) excluding oxygen.

Mo/Cu is between 30:1 and 1:3, and the corresponding molar ratio Mo/(total amount of W and Nb) is between 80:1 and 1:4.

Preferably, the variables should be chosen within the ranges specified with the proviso that the molar proportion of the element Mo, based on the total amount of all elements excluding oxygen in the catalytically active multimetal oxide material (IIIa), is 20 to 80 mol %, the molar ratio of Mo present in the catalytically active multimetal oxide material (IIIa) to V, Mo/V, present in the catalytically active multimetal oxide material (IIIa) is 15:1 to 1:1, the corresponding molar ratio Mo/Cu is 30:1 to 1:3, and the corresponding molar ratio Mo/(total amount of W and Nb) is 80:1 to 1:4.

The first catalyst and second catalyst may take the form, for example, of pellets, beads or rings with a passage hole, which are produced by a tableting machine or an extrusion machine. Otherwise, it may be used with similar activity in a form with catalytic components deposited on a refractory support.

The first catalyst and second catalyst and the production thereof are described in detail, for example, in U.S. Pat. No. 8,232,425 B2.

The second catalytic oxidation reaction in the second reactor is performed at a temperature in the range from 240 to 320° C., an operating pressure in the range from 1.5 to 2.5 bar absolute, and a residence time in the range from 1 to 1.7 seconds.

The product stream of the second catalytic oxidation reaction, as well as any unconverted portion of the alkene and/or any unconverted portion of the gas stream comprising at least one α,β-ethylenically unsaturated aldehyde, comprises at least one α,β-ethylenically unsaturated carboxylic acid that has been formed by partial oxidation of the aldehyde. Thus, the partial oxidation of acrolein leads to acrylic acid, and the partial oxidation of methacrolein to methacrylic acid. The α,β-ethylenically unsaturated carboxylic acid is preferably selected from acrylic acid.

The gas stream produced from the second reactor that comprises at least one α,β-ethylenically unsaturated carboxylic acid, preferably acrylic acid, aside from propylene, acrolein and oxygen, comprises essentially acrylic acid. The carboxylic acid, preferably acrylic acid, is typically obtained by absorption or fractional distillation.

Acrylic acid is absorbed in an absorption liquid suitable for absorption of acrylic acid, for example diphenyl, diphenyl ether, dimethyl phthalate, ethylhexanoic acid, N-methylpyrrolidone, paraffin fractions or mixtures thereof; oligomeric acrylic acids, such as mixtures comprising di-, tri- and tetraacrylic acid, or water. The absorption liquid is contacted with the gas stream comprising at least one α,β-ethylenically unsaturated carboxylic acid in an absorption column in countercurrent, for example after cooling by means of a heat exchanger at a temperature of 100 to 180° C. Suitable absorption columns are, for example, columns with random packing, columns with structured packing, valve tray columns or bubble-cap tray columns. The acrylic acid-laden absorption liquid generally comprises volatile impurities, such as water, acrolein, formaldehyde, formic acid and/or acetic acid. These may be at least partly removed by stripping with a stripping gas, for example nitrogen or air, in a desorption column in countercurrent. The crude acrylic acid is typically obtained by rectificative removal under reduced pressure, e.g. 0.04 to 0.1 bar, for example in a column with random packing or a tray column. The crude acrylic acid is removed as top product or via a side draw in the upper region of the rectification column, and the absorption liquid is appropriately recycled and reused for absorption. When water is used as absorption liquid, the crude acrylic acid is isolated from the aqueous acrylic acid solution by extraction in an extraction column in countercurrent with an extractant, for example ethyl acetate, butyl acetate, ethyl acrylate, 2-butanone or mixtures thereof, and subsequent distillation of the extract.

For fractional condensation, the gas stream comprising at least one α,β-ethylenically unsaturated carboxylic acid is cooled to 100 to 180° C. and appropriately introduced into the lower region of a column having separating internals. As it ascends within the column, it is possible to remove a medium boiler fraction as crude acrylic acid fraction via a suitably mounted collecting tray. This crude acrylic acid fraction can be purified further in a crystallization. The crystallization method is not subject to any restriction.

In all the workup steps, it is possible to add stabilizers and/or polymerization inhibitors for acrylic acid in a manner known per se. An example of a suitable stabilizer is phenothiazine. Examples of suitable polymerization inhibitors are hydroquinone, hydroquinone monomethyl ether, p-nitrosophenol, tert-butylphenols or mixtures thereof.

All plant components that come into contact with reaction gases in the process described are manufactured from materials that are acetic acid-, acrolein- or acrylic acid-resistant under the prevailing reaction conditions.

It has been found that the molybdenum impurities used in the first catalyst have a tendency to sublime under the reaction conditions that exist in the first reactor. The catalyst constituents discharged, in the case of conventional plants having two reactors, enter the second reactor via the connecting conduit together with the reaction gas from the first reactor. They are deposited therein, for example, on inert random packings in the preheating zone and/or on the second catalyst. This constricts the free cross section in the second reactor (fouling) and increases the pressure drop in the course of passage of the reaction gas through the second reactor. The operation of the synthesis at elevated pressure therefore results in losses in acrylic acid selectivity. Once the pressure drop has reached a particular degree, the reactor has to be shut down, and the uppermost layer of the bed or of the inert random packings has to be exchanged (skimming).

According to the invention, this need for maintenance is reduced in that the gas stream comprising at least one α,β-ethylenically unsaturated aldehyde, which entrains some level of discharged catalyst constituents from the first catalyst, after leaving the first reactor and before entering the second reactor, is passed through an exchangeable structure with high specific surface area which is disposed in the connecting conduit. Advantageously, as a result, the catalyst constituents of the first catalyst that are discharged from the first reactor together with the reaction gas do not pass unhindered into the second reactor, but are partly or fully desublimed on the high specific surface area of the exchangeable structure.

"Specific surface area" of the exchangeable structure is understood to mean the surface area provided by the exchangeable structure based on the volume of the exchangeable structure. The "surface area provided by the exchangeable structure" refers to a corresponding surface area in macroscopic terms (geometric surface area), without taking account of any possible roughness of this surface. The "high specific surface area" of the exchangeable structure refers especially to a surface area greater than the surface area of the connecting conduit if the exchangeable structure were absent.

In a further configuration, the microscopic surface area of the exchangeable structure is increased in that the roughness of this surface area is elevated. The average roughness Ra is, for example, greater than 0.35 μm, preferably greater than 1 μm, more preferably not less than 2 μm. The average roughness Ra is, for example, within a range from 2 μm to 3 μm, especially within a range from 2 μm to 2.5 μm.

In one embodiment, the flow rate of the gas stream comprising at least one α,β-ethylenically unsaturated aldehyde is slowed in the region of the exchangeable structure. The slowing of the flow rate is achieved, for example, by an increase in the cross-sectional area of the connecting conduit. The slowing of the flow rate results in a longer dwell time of the gas stream comprising at least one α,β-ethylenically unsaturated aldehyde in the exchangeable structure. A longer dwell time promotes the desublimation of the catalyst constituents discharged.

In one embodiment, the gas stream comprising at least one α,β-ethylenically unsaturated aldehyde, after leaving the first reactor and before passing through the exchangeable structure, is cooled by 80 to 160° C., preferably 110 to 145° C. The cooling is effected, for example, by means of an external cooler disposed in the connecting conduit. The external cooling of the gas stream comprising at least one α,β-ethylenically unsaturated aldehyde, which may comprise catalyst constituents of the first catalyst that are discharged with the reaction gas from the first reactor, facilitates desublimation at the high specific surface area of the exchangeable structure.

In the process of the invention, the desublimation, from a thermodynamic point of view, can be promoted by low temperatures of the gas stream comprising at least one α,β-ethylenically unsaturated aldehyde or by low water concentrations in said gas stream. Since the present oxidation gives rise to water as a by-product, the water concentration can be controlled only to a limited degree. The promoting of desublimation is therefore advantageously achieved by cooling, i.e. at low temperatures, of the gas stream after it leaves the first reactor. However, in the case of excessively low temperatures, there is the risk that higher-boiling secondary components will condense out, which can lead to fouling of plant components. In general, therefore, the catalyst constituents of the first catalyst that are discharged from the first reactor with the reaction gas are partly desublimed at the high specific surface area of the exchangeable structure, while a further portion can also be desublimed, for example, at the inner pipe wall of the connecting conduit between the two reactors.

The exchangeable structure is exchangeable. In one embodiment, the exchangeable structure is exchanged once or periodically while the first reactor (A) and/or second reactor (B) are not being cooled below 150° C. By virtue of the first reactor and/or second reactor not being cooled completely, these may be kept thermally close to the reaction conditions, for example at 150° C. and 1 bar absolute. The temperature here is higher than the melting temperature of the temperature control medium surrounding the reaction tubes (for example of the salt bath). By keeping the salt bath in the molten state, the reaction conditions are very rapidly reattained after the synthesis is restarted. Thus, both the time taken and the need for maintenance can be considerably reduced compared to conventional maintenance or cleaning processes (skimming) (a few hours rather than about 2 weeks), since, for example, it is not necessary to cool the salt melt to room temperature and reheat it to at least 150° C.

A preferred embodiment comprises the production of acrylic acid by two-stage catalytic gas phase oxidation of propylene, wherein propylene is oxidized to acrolein in the first catalytic oxidation reaction, and the acrolein is oxidized further to acrylic acid in the second catalytic oxidation reaction. This process enables the efficient production of the acrylic acid product of value, which finds use on an industrial scale, for example, in polymerizations.

The invention also relates to a plant for producing α,β-ethylenically unsaturated carboxylic acids by two-stage catalytic gas phase oxidation of alkenes, comprising a) a first reactor designed for performance of a first catalytic oxidation reaction of a gas stream comprising at least one alkene in the presence of oxygen over a first catalyst in the form of a multimetal oxide of molybdenum to obtain a gas stream comprising at least one α,β-ethylenically unsaturated aldehyde, b) a second reactor designed for performance of a second catalytic oxidation reaction of the gas stream comprising at least one α,β-ethylenically unsaturated aldehyde in the presence of oxygen over a second catalyst to obtain a gas stream comprising at least one α,β-ethylenically unsaturated carboxylic acid, c) a connecting conduit which is disposed between the first reactor and the second reactor in order to direct the gas stream comprising at least one α,β-ethylenically unsaturated aldehyde into the second reactor, and d) an exchangeable structure with high specific surface area which is disposed in the connecting conduit, and through which the gas stream comprising at least one α,β-ethylenically unsaturated aldehyde can be passed.

"Specific surface area" of the exchangeable structure is understood to mean the surface area provided by the exchangeable structure based on the volume of the exchangeable structure. The "high specific surface area" of the exchangeable structure refers especially to a surface area greater than the surface area of the connecting conduit if the exchangeable structure were absent.

In one embodiment, the exchangeable structure has a specific surface area of at least 400 $m^2/m^3$, preferably at least 600 $m^2/m^3$. The installation of exchangeable structures having a specific surface area of at least 400 $m^2/m^3$ promotes the desublimation of the discharged catalyst constituents and hence reduces the need for maintenance of the plant.

In addition, the structure is chosen such that a minimum pressure drop through the structure occurs. This can be achieved via the installed absolute surface area of the structure (S). This is, for example, at least 350 $m^2$.

In one embodiment, the exchangeable structure has a specific surface area per unit gas volume of at least 600 $m^2/m^3$, preferably at least 800 $m^2/m^3$. "Specific surface area per unit gas volume" of the exchangeable structure is understood to mean the surface area provided by the exchangeable structure past which the gas stream flowing through, for example the acrolein-comprising gas stream, flows directly and which comes into contact with the surface of the structure, based on the void volume of the structure through which the gas stream flows.

The installation of exchangeable structures having a specific surface area per unit gas volume of at least 600 $m^2/m^3$ promotes the desublimation of the discharged catalyst constituents and hence reduces the need for maintenance of the plant.

In one embodiment, the exchangeable structure is a structured packing. The term "structured packing" is understood to mean internals such as, for example, metal plates (trays), metal meshes, metal grids, etc. The trays may, for example, be smooth, corrugated, perforated or embossed. The flow channels of the metal grids may, for example, have a straight or inclined configuration. In general, structured packings offer a high (contact) surface area, but low resistance to gas flow.

The prior art discloses the production of acrylic acid from propylene, wherein catalyst constituents discharged from the reactor are removed in suitable installations, for example at random packings disposed in the reaction tubes. Random packings are not structured packings, but are regarded as unstructured packings. Desublimation of the discharged catalyst constituents on bodies of such random packings (unstructured packing) results in a greater rise in pressure drop than in the case of desublimation on structured packings with the same absolute surface area.

In one embodiment, the exchangeable structure consists of a ceramic. The ceramic is preferably a monolithic ceramic. Monolithic ceramics are capable of withstanding high temperatures and have high erosion resistance, for example by comparison with composite materials having a ceramic matrix. In addition, monolithic ceramics use inexpensive raw materials and can be shaped into particular shapes. The monolithic ceramic may consist, for example, of silicon dioxide ($SiO_2$), silicon nitride ($Si_3N_4$), silicon aluminum oxynitride (SiAlON), silicon carbide (SiC), silicon oxynitride ($Si_2N_2O$), aluminum nitride (AlN), aluminum oxide ($Al_2O_3$), hafnium dioxide ($HfO_2$), zirconium dioxide ($ZrO_2$), silicized silicon carbide (Si—SiC) or other oxides, carbides or nitrides, or a combination thereof, preferably of silicon dioxide ($SiO_2$) and/or aluminum oxide ($Al_2O_3$).

The exchangeable structure especially consists of blocks, preferably of tetragonal blocks. The exchangeable structure typically comprises 1 to 200, preferably 50 to 170, more preferably 100 to 150, blocks. Typically, every tetragonal block has edge lengths of 100 to 200 mm (length) and 100 to 200 mm (width). Tetragonal blocks having long edge lengths are preferred. The depth of the blocks runs in flow direction of the gas stream and is 150 to 350 mm. It is matched to the pressure drop and the total surface area of the exchangeable structure. The blocks are arranged alongside one another. The blocks preferably fill the cross-sectional area of the exchangeable structure. The "cross-sectional area" of the exchangeable structure is understood to mean any area of the exchangeable structure at right angles to the flow direction of the gas stream comprising at least one α,β-ethylenically unsaturated aldehyde that flows through. There are essentially no gaps between the blocks. It is possible to close any gaps in a gas-tight manner, for example with a glass weave. The blocks more preferably completely fill the cross-sectional area of the exchangeable structure.

In one embodiment, the exchangeable structure comprises channels. The channels may especially be formed in the aforementioned blocks. The channels may have different cross sections, for example round, honeycomb-shaped, rectangular and square. Channels with a square cross section are preferred. The longitudinal direction of the channels is in each case aligned in flow direction of the gas stream comprising at least one α,β-ethylenically unsaturated aldehyde. The surfaces of the channels provide the surface area of the exchangeable structure at which the discharged catalyst constituents are desublimed, which reduces the need for maintenance of the plant.

The cross-sectional area of the connecting conduit is completely filled by the exchangeable structure. The gas stream comprising at least one α,β-ethylenically unsaturated aldehyde is especially directed through the channels of the exchangeable structure and hence over the surface area thereof, and cannot flow past the exchangeable structure. More preferably, the gas stream comprising at least one α,β-ethylenically unsaturated aldehyde cannot reach the second reactor without flowing through the channels of the exchangeable structure beforehand. This means that the cross-sectional area of the connecting conduit especially has no gaps. The channels in the blocks of the exchangeable structure are not regarded here as "gaps". "Gaps" are understood to mean, for example, openings between the outer end of the exchangeable structure and the housing, or openings between two blocks, if they are not aligned sufficiently closely that their outer walls are in contact.

In one embodiment, the connecting conduit has an installed housing with the exchangeable structure disposed therein. The housing is of gastight construction. The exchangeable structure is especially mounted releasably in the housing, such that it can be exchanged. For example, the exchangeable structure can be removed and replaced by a new exchangeable structure.

Alternatively or additionally, the housing may be parted from the remaining sections of the connecting conduit and removed. For this purpose, the housing has a connection port at each end, via which the housing is releasably connected to the connecting conduit via screws and can be secured by flanges. In that case, the housing together with the exchangeable structure may be replaced by a new housing together with a new exchangeable structure. The exchangeable structure may then be mounted in a nonreleasable manner in the housing. The arrangement of the exchangeable structure in a housing installed in the connecting conduit enables simple and rapid exchange of the exchangeable structure disposed in the housing, in that a used exchangeable structure disposed in the housing is replaced by a new structure or a new housing comprising the exchangeable structure.

Typically, the exchangeable structure lies on a support element mounted beneath the exchangeable structure in the housing. Typical support elements include, for example, grids and meshes. The openings of the support elements have greater cross-sectional areas than the cross-sectional areas of the channels of the structured packing. The support element serves to prevent any shift in the exchangeable structure in the housing or in the direction of the connecting conduit, for example through slippage.

In one embodiment, the cross-sectional area of the housing of the exchangeable structure is greater than the cross-sectional area of the connecting conduit. The "cross-sectional area" of the housing is understood to mean any area of the housing at right angles to the flow direction of the gas stream comprising at least one α,β-ethylenically unsaturated aldehyde that flows through. The cross-sectional area of the housing of the exchangeable structure is preferably at least 25% larger than the cross-sectional area of the connecting conduit, more preferably at least 150% larger. The embodiment in which the cross-sectional area of the housing of the exchangeable structure is greater than the cross-sectional area of the connecting conduit allows the pressure drop in the process of the invention to be kept low. Embodiments in which the pressure drop can be minimized result in a higher selectivity for acrylic acid in the oxidation of propylene to acrylic acid and are therefore particularly preferred.

Moreover, the surface area provided for sublimation of the catalyst constituents is increased via greater cross-sectional areas. In particular, the surfaces are provided parallel to one another, such that no pressure drop occurs even in the case of adsorption of catalyst constituents at the surface. As a result, the cross section remains sufficient for the passage of the gas over a prolonged period of time. This advantageously extends the maintenance intervals or reduces the need for maintenance of the plant.

In one embodiment, the plant comprises a cooler for cooling of the gas stream comprising at least one α,β-ethylenically unsaturated aldehyde after it leaves the first reactor and before it passes through the exchangeable structure. The cooling of the gas stream comprising at least one α,β-ethylenically unsaturated aldehyde, which may comprise catalyst constituents of the first catalyst that are discharged with the reaction gas from the first reactor, facilitates partial or complete desublimation at the high specific surface area of the exchangeable structure.

Unless stated otherwise, the above-described embodiments, elucidations and preferences apply equally to the process of the invention and the plant of the invention.

BRIEF DESCRIPTION OF FIGURES

The present invention is now elucidated in detail by the appended drawings using the example of the production of acrylic acid from propylene.

With reference to FIGS. 1 and 2, a working example of the plant of the invention is elucidated:

FIG. 1 shows a plant of the invention for catalytic gas phase oxidation of propylene to acrylic acid. The plant comprises a salt bath-moderated first shell-and-tube heat exchange reactor A, which has reaction tubes R1 filled with a first catalyst K1. A connecting conduit V connects the first shell-and-tube heat exchange reactor A to a salt bath-moderated second shell-and-tube heat exchange reactor B. The second shell-and-tube heat exchange reactor B comprises reaction tubes R2 filled with a second catalyst K2.

The connecting conduit V has a cooler K' between the first shell-and-tube heat exchange reactor A and the second shell-and-tube heat exchange reactor B. The connecting conduit V also has a housing G with an exchangeable structure S disposed therein. The housing G is part of the connecting conduit V. It is inserted into the connecting conduit V between the cooler K' and the second shell-and-tube heat exchange reactor B. The connecting conduit V between the first shell-and-tube heat exchange reactor A and the housing G has a diameter of 1.4 m. The connecting conduit V between the housing G and the second shell-and-tube heat exchange reactor V has a diameter of 1.6 m. The housing comprising the exchangeable structure S has a diameter of 2 m.

Figure 2:
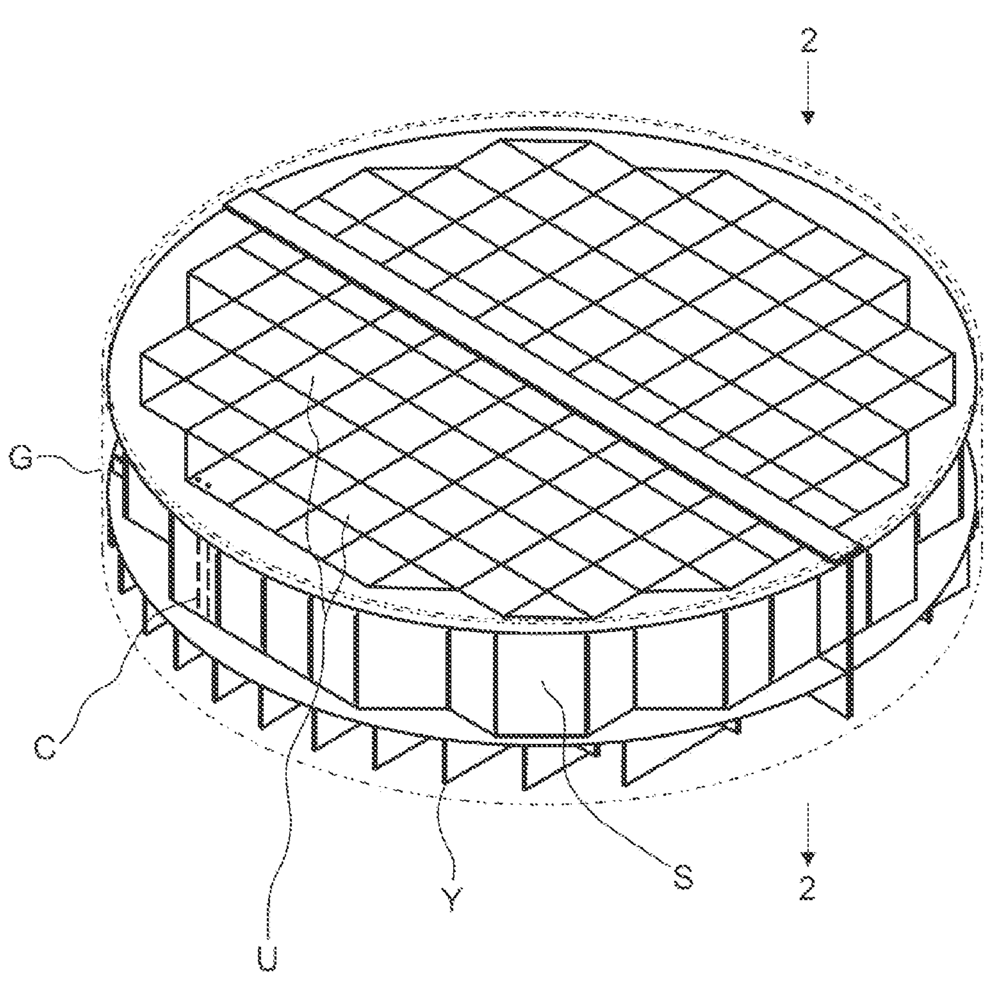
FIG. 2 shows a schematic perspective diagram of a cross section of the exchangeable structure with high specific surface area.

The exchangeable structure S disposed in the housing G has blocks U and channels C formed in flow direction of the acrolein-comprising gas stream 2 that flows through it. A schematic diagram of a cross section of the exchangeable structure S is shown in FIG. 2. The channels C are indicated as dotted lines in FIG. 2. The surfaces of the channels provide a high specific surface area of the exchangeable structure by comparison with the surface area provided by the connecting conduit on its own. This high specific surface area is 600 $m^2/m^3$. The specific surface area per unit gas volume is 800 $m^2/m^3$. The specific surface area is the geometric surface area neglecting the increases in surface area on account of roughness. The average roughness Ra of the structure is within a range from 2 μm to 2.5 μm.

The blocks of the exchangeable structure S lie on a grid Y in the housing G. They essentially completely fill the cross section of the housing G and hence of the connecting conduit V. Any gaps are filled, for example, by glass weave. The housing G has one connection port at one end and one at the other end, via which the housing G is releasably connected to other sections of the connecting conduit V via screws and is secured by flanges.

Figure 1:
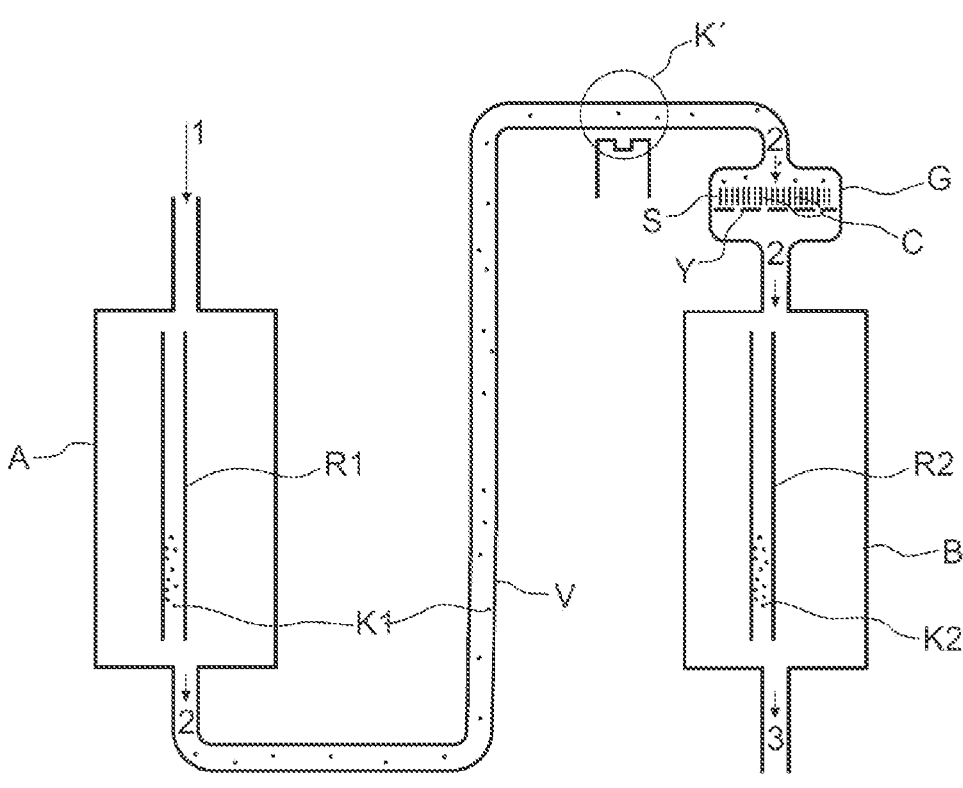
FIG. 1 shows a schematic of a working example of the plant of the invention for production of acrylic acid by two-stage catalytic gas phase oxidation of propylene.

There follows a description of a working example of the process of the invention, wherein further details of the working example of the plant of the invention are elucidated:

A propylene-comprising gas stream 1 is introduced into the first shell-and-tube heat exchange reactor A and flows through the reaction tubes R1 filled with the first catalyst K1. In the first shell-and-tube heat exchange reactor A, propylene is reacted with atmospheric oxygen over the first catalyst K1 in a first catalytic oxidation reaction to give acrolein. The first catalyst K1 used is a multimetal oxide of molybdenum. A resulting gas stream 2 that comprises essentially acrolein as well as unconverted atmospheric oxygen, as shown in FIG. 1 by the arrow at the lower end of the first shell-and-tube heat exchange reactor A, leaves the first shell-and-tube heat exchange reactor A via connecting conduit V. Under the prevailing reaction conditions of 300 to 400° C. and 2 to 3 bar absolute in the first shell-and-tube heat exchange reactor A, constituents of the first catalyst K1 sublime to some degree and are discharged into the connecting conduit V by the acrolein-comprising gas stream 2.

The acrolein-comprising gas stream 2, before reaching the second shell-and-tube heat exchange reactor B, passes through the cooler K', which cools it down from 350° C. to 240° C. In addition, the acrolein-comprising gas stream 2, after leaving the cooler K' and before reaching the exchangeable structure S, is cooled down by heat loss in the pipeline from 240° C. to 150° C. The acrolein-comprising gas stream 2, as illustrated in FIG. 1 by the arrows, is guided through the exchangeable structure S in that it flows through the channels C of the blocks U of the exchangeable structure S. The sublimed constituents of the first catalyst K1 that are present in the acrolein-comprising gas stream 2 are subsequently partly or fully desublimed at the surface of the channels C in the blocks U of the exchangeable structure S. The resulting acrolein-comprising gas stream 2 that has been essentially freed of sublimed constituents of the first catalyst K1 then leaves the exchangeable structure S via connecting conduit V (not shown in FIG. 2).

Subsequently, the acrolein-comprising gas stream 2 is introduced into and flows through the second shell-and-tube heat exchange reactor B, as indicated in FIG. 1 by the arrow at the reactor inlet of the second shell-and-tube heat exchange reactor B. In the second shell-and-tube heat exchange reactor B, the acrolein is subjected to a second oxidation reaction in the presence of atmospheric oxygen over the second catalyst K2, forming acrylic acid from acrolein. The second catalyst K2 used is a multimetal oxide of molybdenum. A resulting acrylic acid-comprising gas stream 3 comprises essentially acrylic acid as well as propylene, acrolein and oxygen, and is removed at the outlet from the second shell-and-tube heat exchange reactor B.

With increasing deposition of sublimed constituents of the first catalyst K1 in the channels C of the exchangeable structure S, the cross section of the channels C is reduced by the accumulation of the desublimed constituents of the first catalyst K1. This can lead to a rise in pressure in the first shell-and-tube heat exchange reactor A, which necessitates an exchange of the exchangeable structure (maintenance). During the lifetime of the first catalyst 1 and/or of the second catalyst 2, the exchangeable structure may be exchanged once or periodically. The exchange follows interruption of the synthesis in the first shell-and-tube heat exchange reactor A and second shell-and-tube heat exchange reactor B by shutdown of the plant (standby). For this purpose, the reactors are typically kept at 1 bar absolute and about 150° C. The stated temperature is higher than the melting temperature of the salt bath. By keeping the salt bath in the molten state, the reaction conditions are very rapidly reattained after the synthesis is restarted. Cooling of the salt melt to room temperature and reheating to at least 150° C., by comparison, is significantly more time-consuming and resource-intensive.

Subsequently, the housing G comprising the exchangeable structure S is removed. For this purpose, the screws of the flanges that connect the housing G to the connecting conduit V are released. Subsequently, the connecting conduit V is opened at the connection ports mounted at the ends of the housing G. The housing G comprising the used exchangeable structure S is lifted away with a crane. Subsequently, a new housing G with a new exchangeable structure is inserted, and the connecting conduit V is sealed gastight again with the flanges and screwed in. In an alternative working example, a bypass or two structures are connected in parallel, in which case only one at a time is in operation and it is possible to switch to the other during operation. Subsequently, the synthesis in the first shell-and-tube heat exchange reactor A and second shell-and-tube heat exchange reactor B can be restarted.

The arrangement of the exchangeable structure in a housing installed in the connecting conduit enables simple and rapid exchange of the exchangeable structure disposed in the housing. Moreover, the exchange is very much simpler than in the processes described to date in the prior art. To date, the discharged catalyst constituents have been deposited on surfaces (for example of beds) in the second shell-and-tube heat exchange reactor B. When there was a rise in pressure drop, it was consequently necessary to stop the process in order to cool the reactor, to open it, and to be able to conduct maintenance in the form of cleaning of the individual reaction tubes. The need for maintenance of the plant of the invention is consequently many times smaller.

LIST OF REFERENCE NUMERALS

1 gas stream comprising at least one alkene
2 gas stream comprising at least one α,β-ethylenically unsaturated aldehyde
3 gas stream comprising at least one α,β-ethylenically unsaturated carboxylic acid
A first shell-and-tube heat exchange reactor
B second shell-and-tube heat exchange reactor
C channel
G housing
K' cooler
K1 first catalyst
K2 second catalyst
R1 reaction tube (in the first shell-and-tube heat exchange reactor A)
R2 reaction tube (in the second shell-and-tube heat exchange reactor B)
S exchangeable structure
U block
V connecting conduit
Y grid

The invention claimed is:

1. A process for producing α,β-ethylenically unsaturated carboxylic acids by two-stage catalytic gas phase oxidation of alkenes, in which a) a gas stream comprising at least one alkene, in a first reactor in the presence of oxygen, is subjected to a first catalytic oxidation reaction over a first catalyst in the form of a multimetal oxide of molybdenum to obtain a gas stream comprising at least one α,β-ethylenically unsaturated aldehyde, b) the gas stream comprising at least one α,β-ethylenically unsaturated aldehyde is directed through a connecting conduit into a second reactor and c) the gas stream comprising at least one α,β-ethylenically unsaturated aldehyde, in the second reactor in the presence of oxygen, is subjected to a second catalytic oxidation reaction over a second catalyst to obtain a gas stream comprising at least one α,β-ethylenically unsaturated carboxylic acid, which comprises directing the gas stream comprising at least one α,β-ethylenically unsaturated aldehyde through an exchangeable structure with high specific surface area which is disposed in the connecting conduit.

2. The process according to claim 1, in which the flow rate of the gas stream comprising at least one α,β-ethylenically unsaturated aldehyde is slowed in the region of the exchangeable structure.

3. The process according to claim 1, in which the gas stream comprising the at least one α,β-ethylenically unsaturated aldehyde, after leaving the first reactor and before passing through the exchangeable structure, is cooled by 80 to 160° C.

4. The process according to claim 1, in which the exchangeable structure is exchanged once or periodically while the first reactor and/or second reactor is not being cooled below 150° C.

5. The process according to claim 1 for production of acrylic acid by two-stage catalytic gas phase oxidation of propylene.

6. A plant for producing α,β-ethylenically unsaturated carboxylic acids by two-stage catalytic gas phase oxidation of alkenes, comprising a) a first reactor designed for performance of a first catalytic oxidation reaction of a gas stream comprising at least one alkene in the presence of oxygen over a first catalyst in the form of a multimetal oxide of molybdenum to obtain a gas stream comprising at least one α,β-ethylenically unsaturated aldehyde, b) a second reactor designed for performance of a second catalytic oxidation reaction of the gas stream comprising at least one α,β-ethylenically unsaturated aldehyde in the presence of oxygen over a second catalyst to obtain a gas stream comprising at least one α,β-ethylenically unsaturated carboxylic acid, c) a connecting conduit which is disposed between the first reactor and the second reactor in order to direct the gas stream comprising at least one α,β-ethylenically unsaturated aldehyde into the second reactor, and d) an exchangeable structure with high specific surface area which is disposed in the connecting conduit, and through which the gas stream comprising at least one α,β-ethylenically unsaturated aldehyde can be passed.

7. The plant according to claim 6, in which the exchangeable structure has a specific area per unit gas volume of at least 400 $m^2/m^3$.

8. The plant according to claim 6, in which the exchangeable structure has a specific surface area per unit gas volume of at least 600 $m^2/m^3$.

9. The plant according to claim 6, in which the exchangeable structure is a structured packing.

10. The plant according to claim 6, in which the exchangeable structure consists of a ceramic.

11. The plant according to claim 6, in which the exchangeable structure comprises channels.

12. The plant according to claim 6, in which the connecting conduit has an installed housing, and the exchangeable structure is disposed within the housing.

13. The plant according to claim 12, in which the cross-sectional area of the housing of the exchangeable structure is greater than the cross-sectional area of the connecting conduit.

14. The plant according to claim 6, in which the first reactor and/or second reactor is a fixed bed shell-and-tube heat exchange reactor.

15. The plant according to claim 6, also comprising a cooler for cooling of the gas stream comprising at least one α,β-ethylenically unsaturated aldehyde after it leaves the first reactor and before it passes through the exchangeable structure.

* * * * *